United States Patent
Geveci

(10) Patent No.: US 8,881,508 B2
(45) Date of Patent: Nov. 11, 2014

(54) SCR CONTROL SYSTEM UTILIZING A DIFFERENTIAL NH₃ AND NOₓ MEASUREMENT USING AN EXHAUST GAS SENSOR COUPLED WITH A MICRO SCR CATALYST

(71) Applicant: Cummins Inc., Columbus, IN (US)

(72) Inventor: Mert Geveci, Albany, NY (US)

(73) Assignee: Commins Inc., Columbus, IN (US)

( * ) Notice: Subject to any disclaimer, the term of this patent is extended or adjusted under 35 U.S.C. 154(b) by 98 days.

(21) Appl. No.: 13/664,787

(22) Filed: Oct. 31, 2012

(65) Prior Publication Data

US 2013/0104530 A1 May 2, 2013

Related U.S. Application Data

(60) Provisional application No. 61/553,710, filed on Oct. 31, 2011.

(51) Int. Cl.
| | |
|---|---|
| *F01N 3/00* | (2006.01) |
| *F01N 3/10* | (2006.01) |
| *F01N 13/00* | (2010.01) |
| *B01D 53/94* | (2006.01) |
| *G01N 27/407* | (2006.01) |
| *F01N 3/20* | (2006.01) |

(52) U.S. Cl.
CPC ............. *B01D 53/9409* (2013.01); *Y02T 10/24* (2013.01); *F01N 2560/026* (2013.01); *F01N 13/0093* (2013.01); *F01N 2900/0408* (2013.01); *F01N 2900/1404* (2013.01); *F01N 2410/00* (2013.01); *F01N 3/106* (2013.01); *B01D 53/9495* (2013.01); *F01N 2560/021* (2013.01); *F01N 2570/18* (2013.01); *B01D 2251/2062* (2013.01); *G01N 27/407* (2013.01); *F01N 2610/02* (2013.01); *B01D 2255/9032* (2013.01); *F01N 3/208* (2013.01); *F01N 2900/1616* (2013.01); *F01N 2560/06* (2013.01); *B01D 2251/2067* (2013.01); *B01D 2255/9035* (2013.01)
USPC .................. 60/286; 60/276; 60/288; 60/295; 60/301

(58) Field of Classification Search
USPC .................. 60/276, 286, 288, 295, 301, 303; 422/108, 110, 111
See application file for complete search history.

(56) References Cited

U.S. PATENT DOCUMENTS

| | | | |
|---|---|---|---|
| 7,712,307 B2 | 5/2010 | Braun et al. | |
| 7,776,280 B2 | 8/2010 | Telford | |
| 7,810,316 B2 | 10/2010 | Salemme et al. | |
| 7,832,200 B2 | 11/2010 | Kesse et al. | |
| 2009/0266063 A1* | 10/2009 | Gandhi et al. | 60/301 |
| 2011/0011065 A1* | 1/2011 | Knuth | 60/295 |
| 2011/0041480 A1* | 2/2011 | Yasui et al. | 60/286 |
| 2011/0072798 A1* | 3/2011 | Herman | 60/286 |
| 2011/0265452 A1 | 11/2011 | Geveci et al. | |
| 2012/0017567 A1 | 1/2012 | Geveci et al. | |
| 2012/0017568 A1 | 1/2012 | Geveci et al. | |
| 2012/0180457 A1* | 7/2012 | Liu et al. | 60/276 |
| 2012/0233986 A1 | 9/2012 | Geveci et al. | |

* cited by examiner

*Primary Examiner* — Audrey K Bradley
(74) *Attorney, Agent, or Firm* — Krieg DeVault LLP

(57) ABSTRACT

Systems and method are disclosed in which a portion of an exhaust gas stream is received into an exhaust outlet flow path downstream of a first selective catalytic reduction (SCR) catalyst and upstream of a second SCR catalyst. The removed portion is treated with a diagnostic SCR catalyst element and an NH₃ concentration composition of the treated removed portion is determined. The NH₃ concentration is used to control injection of reductant upstream of the first SCR catalyst.

33 Claims, 7 Drawing Sheets

| INLET VARIABILITY | OUTLET VARIABILITY | ACTUATOR MODIFICATION |
|---|---|---|
| HIGH | HIGH | NOMINAL OR INCREASED |
| HIGH | LOW | NOMINAL OR INCREASED |
| LOW | HIGH | DECREASED |
| LOW | LOW | NOMINAL |

SCR CONTROL SYSTEM UTILIZING A DIFFERENTIAL $NH_3$ AND $NO_x$ MEASUREMENT USING AN EXHAUST GAS SENSOR COUPLED WITH A MICRO SCR CATALYST

CROSS-REFERENCE TO RELATED APPLICATIONS

This application claims the benefit of the filing date of Provisional Application Ser. No. 61/553,710 filed on Oct. 31, 2011, which is incorporated herein by reference. This application is also related to U.S. Provisional Patent Application Ser. No. 61/553,700 filed on Oct. 31, 2011, and Utility patent application Ser. No. 13/664,515 filed on the same date as the present application now U.S. Pat. No. 8,617,498 B2, each of which is entitled "DIFFERENTIAL NH3 AND NOX MEASUREMENT USING AN EXHAUST GAS SENSOR COUPLED WITH A MICRO SCR CATALYST," and each of which is incorporated herein by reference in its entirety.

BACKGROUND

The technical field generally relates to SCR aftertreatment systems for internal combustion engines. SCR aftertreatment systems are effective at treating engine $NO_x$ emissions with a high conversion of $NO_x$. SCR aftertreatment systems operate with the addition of urea or $NH_3$ (reductant) to the system, and react the reductant with the $NO_x$, to reduce the $NO_x$. The addition of any excess reductant to the system consumes the reductant without the benefit of $NO_x$ reduction, increasing the operating cost of the system. Additionally, the excess reductant may be slipped from the system, causing undesired emissions, odors, and/or irritation. Where it is not allowable for the reductant to slip but control of the reductant addition amounts is not acceptably precise, a cleanup oxidation catalyst downstream of the SCR catalyst may be utilized, which can reduce reductant slip amounts but increases system acquisition and maintenance costs. Nevertheless, precise control of the reductant addition is difficult. Many SCR catalyst formulations exhibit $NH_3$ storage and release dynamics, and the determination of the instantaneous engine-out $NO_x$ amount is difficult to determine in a commercially viable mobile application. Further, most currently available $NO_x$ sensors have cross-sensitivity to $NH_3$, complicating the direct measurement of $NO_x$ and the separation of $NO_x$ from $NH_3$ detection. Therefore, further technological developments are desirable in this area.

SUMMARY

Systems and methods are disclosed that include directing a portion of an exhaust gas stream into an exhaust outlet flow path downstream of a first selective catalytic reduction (SCR) catalyst and upstream of a second SCR catalyst. The removed portion is treated with a diagnostic SCR catalyst element and an $NH_3$ concentration composition of the treated removed portion is determined. The $NH_3$ concentration is used to control injection of reductant upstream of the first SCR catalyst. Further embodiments, forms, objects, features, advantages, aspects, and benefits shall become apparent from the following description and drawings.

DESCRIPTION OF ILLUSTRATIVE EMBODIMENTS

Figure 1A:
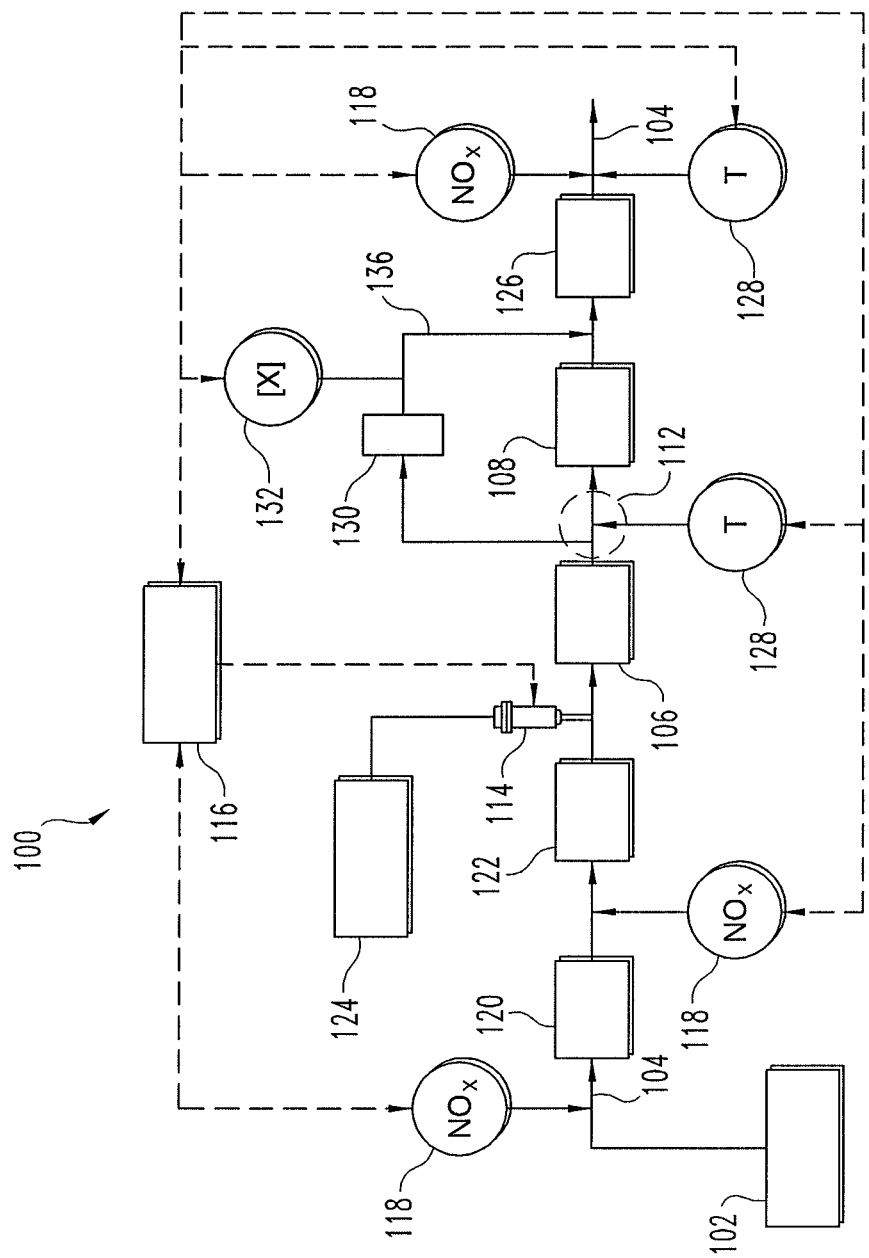
FIG. 1A is a schematic block diagram of a system for control of a selective catalytic reduction system.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

Referencing FIG. 1A, an exemplary system 100 for control of a selective catalytic reduction (SCR) aftertreatment system is shown. The exemplary system 100 includes an internal combustion engine 102, an exhaust conduit 104 fluidly coupled to the internal combustion engine 102, a first SCR catalyst 106 fluidly coupled to the exhaust conduit 104, and a second SCR catalyst 108 fluidly coupled to the exhaust conduit 104 at a position downstream of the first SCR catalyst 106.

The system 100 further includes a diagnostic SCR catalyst element 130 receiving a portion of the exhaust gas stream 104 through the exhaust outlet flow path 136. The diagnostic SCR catalyst element 130 is sized to react all or a portion of the $NO_3$ and $NH_3$ in the exhaust outlet flow path 136. Where the diagnostic SCR catalyst element 130 reacts all of the $NO_x$ and $NH_3$, until the limiting reagent is consumed, the remaining reagent detected at the composition sensor 132 will be either the remaining $NO_x$ or any remaining $NH_3$. At many operating conditions, the controller 116 controls a reductant injector (doser) 114 to provide excess reductant (e.g. from a model of the engine-out $NO_x$, from a detected engine-out $NO_x$ amount, etc.), such that in the exhaust outlet flow path 136 the limiting reagent is $NO_x$ and the composition sensor 132 is determining an excess $NH_3$ amount.

Where the composition sensor 132 is determining remaining $NO_x$, for example when the $NH_3$ is the limiting reagent at the diagnostic SCR catalyst 130, the $NH_3$ depletion condition may be determined as an expected effect (e.g. when the controller 116 commands the reductant injector 114 to provide less than the reductant required to reduce the engine-out $NO_x$), or the $NH_3$ depletion condition may be deduced by a reversal in the expected composition response to a reductant injection increase. In one example, an injection rate increase provides a detected $NO_x$ decrease, which can then be interpreted as increased $NO_x$ conversion resulting from the reductant injection increase, even where it might have been originally expected that the injection rate increase would result in an increased excess $NH_3$ amount and thereby a detected $NH_3$ increase. In certain embodiments, where $NH_3$ is the limiting reagent and the composition sensor 132 is detecting a $NO_x$ amount, the system 100 includes determining an excess $NH_3$ amount as a negative value, for example based upon an amount of $NH_3$ that would need to be provided to reduce the remaining $NO_x$ detected at the sensor 132.

The system includes the compositional sensor 132 disposed in the exhaust outlet flow path 136 at a position downstream of the diagnostic SCR catalyst element 130. The compositional sensor 132 determines $NH_3$ concentration and/or a $NO_x$ concentration in the exhaust outlet flow path 136. Certain sensors known in the art have a cross-sensitivity between $NH_3$ and $NO_x$ determination, and such sensors are usable herein. In certain embodiments, a sensor that determines $NH_3$ without cross-sensitivity to $NO_x$ may also be utilized as a compositional sensor 132.

In certain embodiments, the system 100 includes the diagnostic SCR catalyst 130 being a micro SCR catalyst and/or a differential SCR catalyst. Where the diagnostic SCR catalyst 130 is a differential catalyst, the diagnostic SCR catalyst 130 reacts only a portion of the incident $NO_x$ and $NH_3$ during many operating conditions. The concentration of the $NH_3$ is determinable with a differential catalyst, based partially on an upstream composition value (e.g. from a second composition sensor positioned upstream in the exhaust outlet flow path 136, not shown), a reaction rate model, or other determination mechanism. The change in concentration of the $NH_3$, along with the final concentration of $NH_3$, can be correlated to an excess amount of $NH_3$, either by reaction rate modeling or by a pre-calibrated model or lookup table. In certain embodiments, the exemplary diagnostic SCR catalyst 130 is sized to react substantially all of the limiting reagent between $NO_x$ and $NH_3$ present in the exhaust outlet flow path 136.

The system 100 further includes a reductant doser (injector) 114 operationally coupled to the exhaust conduit 104 at a position upstream of the first SCR catalyst 106, and a controller 116 having a number of modules structured to functionally execute operations for controlling an SCR aftertreatment system.

The first SCR catalyst 106 is illustrated downstream of a diesel oxidation catalyst (DOC) 120 and a diesel particulate filter (DPF) 122. Any of these components may be present or missing, catalyzed or not catalyzed, and may be arranged in alternate order. Further, certain components or all components may be provided in the same or separate housings.

The first SCR catalyst 106 and the second SCR catalyst 108 may occur within the same catalyst brick, with the position of the inlet tm flow path 136 defining the separation point between the first SCR catalyst and the second SCR catalyst. The reductant injector 114 is fluidly coupled to a reductant source 124 such as a reductant storage tank. The reductant is any type of reductant utilized in an SCR aftertreatment system that results in ammonia being utilized as the final reductant—including at least ammonia (gaseous or aqueous) and urea. Certain operations described herein apply to $NO_x$ reduction generally and are not specific to SCR systems. Where the $NO_x$ reduction operations are not specific to SCR systems, hydrocarbon or other reductants may be utilized.

The system 100 may include an ammonia oxidation catalyst (AMOX) 126 downstream of the second SCR catalyst 108. In certain embodiments, the AMOX 126 may not be present, or the AMOX 126 may be commingled with the second SCR catalyst 108 (or the last SCR catalyst, where multiple SCR catalysts are present), for example with a washcoat applied toward the rear portion of the second SCR catalyst 108 that is responsive to at least partially oxidize ammonia.

The exemplary system 100 further includes various additional sensors. The illustrated sensors include a $NO_x$ sensor 118 positioned upstream of the first SCR catalyst 106, a second $NO_x$ sensor 118 positioned downstream of the second SCR catalyst 108, a temperature sensor 128 positioned between the first and second SCR catalysts 106 and 108, and/or the temperature sensor 128 positioned downstream of the AMOX 126 catalyst. The illustrated sensors are exemplary only, and may be re-positioned, removed, substituted, and other sensors may be present that are not illustrated in FIG. 1. Certain embodiments of the system do not include a $NO_x$ sensor 118 present upstream of the first SCR catalyst 106, a $NO_x$ sensor 118 present downstream of the second SCR catalyst 108, or both. Further, certain sensors may instead be virtual sensors that are calculated from other parameters available to the system, or values that would be indicated by sensors may instead be supplied to a computer readable memory location, via a datalink or network communication, or otherwise be made available to the system where the sensor providing the sensed parameter is not a part of the defined system.

Figure 1B:
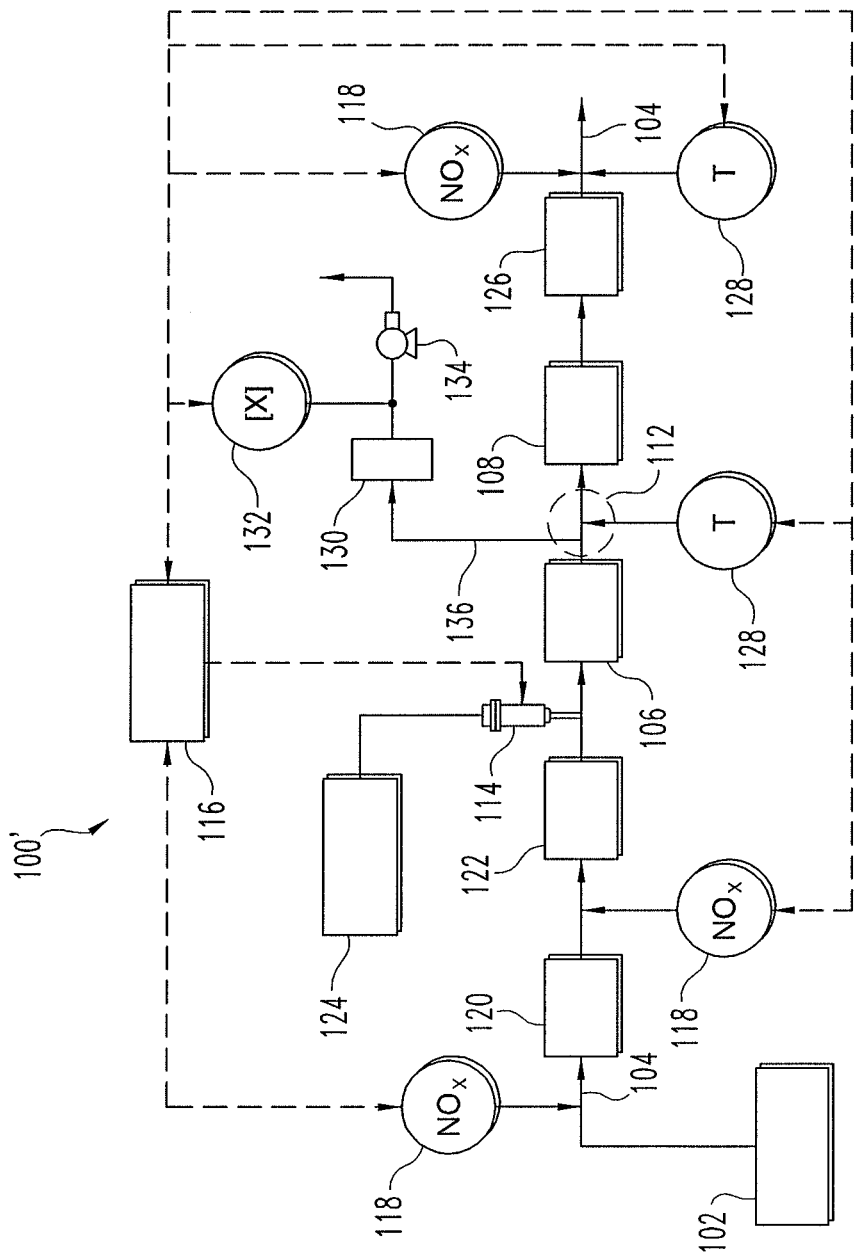
FIG. 1B is a schematic block diagram of another embodiment system for control of a selective catalytic reduction system.

Referencing FIG. 1B, in another embodiments the system 100' includes a vacuum pump 134 that pulls the portion of the exhaust gas stream through the exhaust outlet flow path 136. In certain further embodiments, the vacuum pump 134 vents the exhaust outlet flow path 136, providing the effluent of the exhaust outlet flow path 136, possibly after other treatment, to the ambient environment. Additionally or alternatively, the vacuum pump 134 may provide the effluent of the exhaust outlet flow path 136 to any position downstream of the exhaust outlet flow path 136 inlet, including upstream or downstream of the second SCR catalyst 108 and/or the AMOX 126 catalyst.

Figure 5:
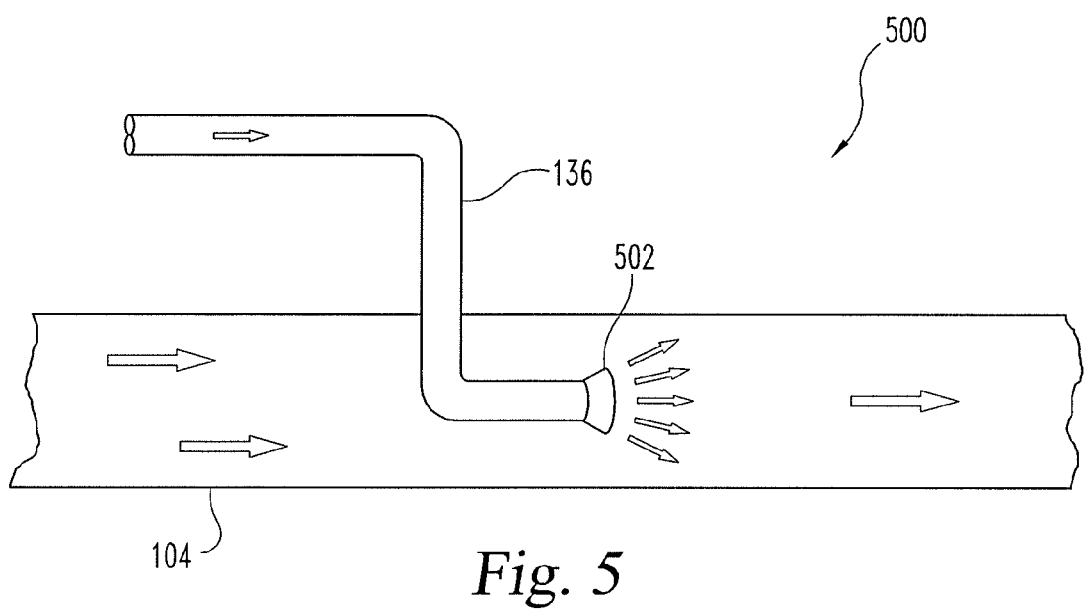
FIG. 5 is a schematic diagram of an outlet of the exhaust outlet flow path to the exhaust stream.

Referencing FIG. 5, an additional or alternative embodiment of an apparatus 500 for enhancing flow through the exhaust outlet flow path 136 is depicted. The outlet of the exhaust outlet flow path 136 includes a flared portion 502. The flared portion 502, with the gases flowing in the exhaust flow path 104, provides a pressure environment where fluid is drawn through the exhaust outlet flow path 136 and returned to the exhaust flow path 104. Additionally or alternatively, certain exemplary embodiments include a means for pulling (or otherwise flowing, pumping, drawing, driving, actively moving, etc.) the portion of the exhaust gas stream through the exhaust outlet flow path 136. Exemplary and non-limiting means for pulling the portion of the exhaust gas stream through the exhaust outlet flow path include a pump, a venturi injector (e.g. the exhaust flow path 104 comprising a venturi flow configuration at the position where the exhaust outlet flow path 136 re-enters the exhaust flow path 104), a flared pipe outlet (e.g. as illustrated in FIG. 5), and/or a fluid conduit configuration that induces a low pressure at a position downstream of the diagnostic SCR catalyst element 130.

In certain embodiments, the system 100 further includes a controller 116 structured to perform certain operations to control a reductant dosing for an SCR system. In certain embodiments, the controller 116 forms a portion of a processing subsystem including one or more computing devices having memory, processing, and communication hardware. The controller 116 may be a single device or a distributed device, and the functions of the controller 116 may be performed by hardware or software.

In certain embodiments, the controller 116 includes one or more modules structured to functionally execute the operations of the controller. In certain embodiments, the controller 116 includes an $NH_3$ target module, $NH_3$ determination module, an $NH_3$ error module, a dosing amount module, a response bounding module, a dosing control module, a $NO_x$ trimming module, a response dampening module, and/or an NH₃ fill-up module. The description herein including modules emphasizes the structural independence of the aspects of the controller, and illustrates one grouping of operations and responsibilities of the controller. Additionally or alternatively, the controller 116 includes an NH₃ determination module, a dosing amount module, and/or a dosing control module. Other groupings that execute similar overall operations are understood within the scope of the present application. Modules may be implemented in hardware and/or software on computer readable medium, and modules may be distributed across various hardware or software components. More specific descriptions of certain embodiments of controller operations are included in the sections referencing FIGS. 2A and 2B.

Interpreting, as utilized herein, includes receiving values by any method known in the art, including at least receiving values from a datalink or network communication, receiving an electronic signal (e.g. a voltage, frequency, current, or PWM signal) indicative of the value, receiving a software parameter indicative of the value, reading the value from a memory location on a computer readable medium, receiving the value as a run-time parameter by any means known in the art, and/or by receiving a value by which the interpreted parameter can be calculated, and/or by referencing a default value that is interpreted to be the parameter value.

Figure 2A:
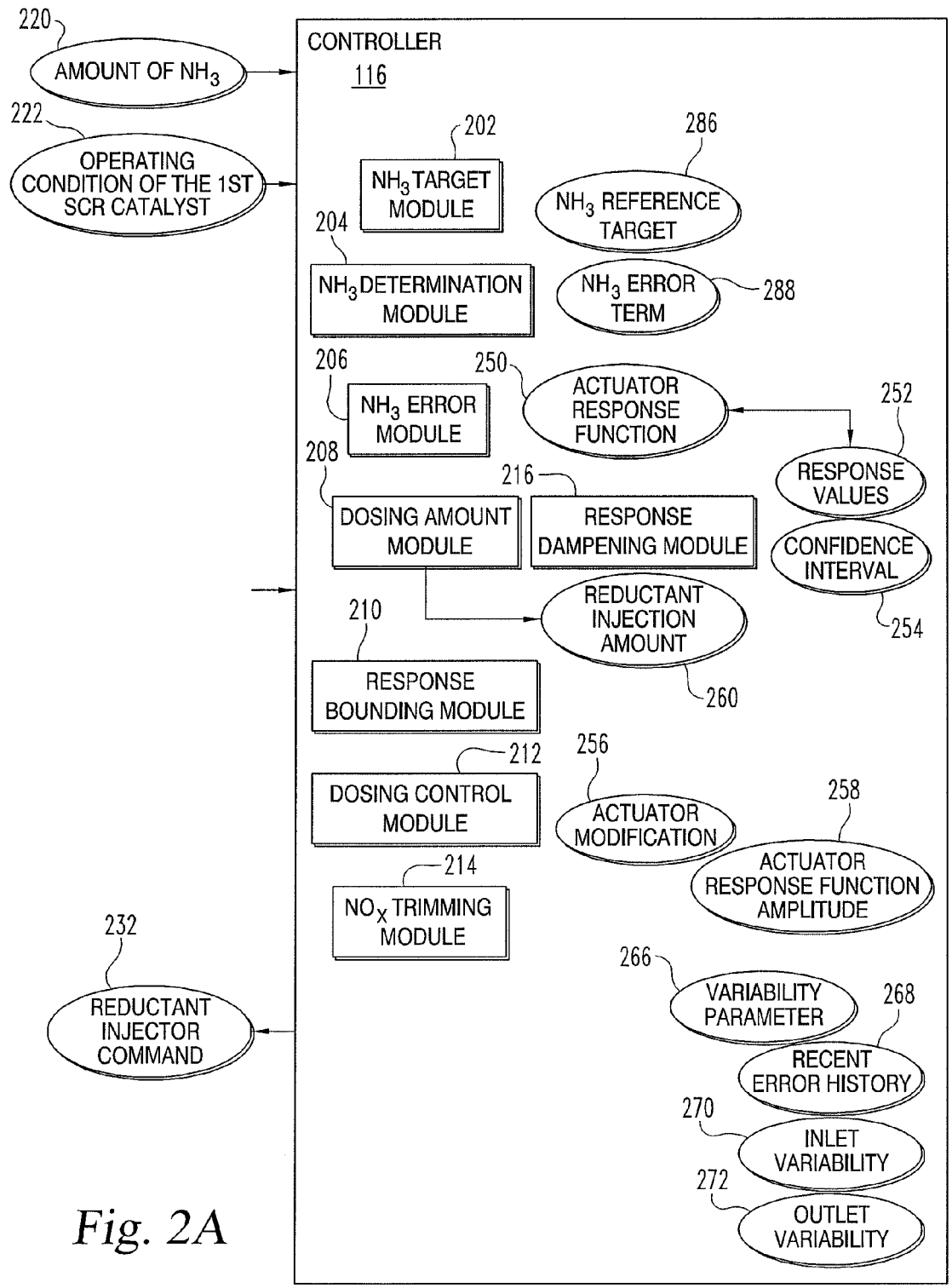
FIG. 2A is a schematic view of a controller that functionally executes certain operations to control a selective catalytic reduction system.

FIG. 2A is an exemplary controller 116 for executing operations to control an SCR aftertreatment system. Certain embodiments of the controller 116 may not utilize all of the modules or reference all of the data illustrated in FIG. 2A. As further shown in FIG. 2B, the controller 116 includes an ammonia determination module 204 that determines an amount of NH₃ 220 present at the first exhaust gas position. The amount of ammonia 220 is determined in response to ammonia composition sensor 132 positioned downstream of diagnostic SCR catalyst element 130 that treats a flow of gas removed from the exhaust conduit at a position approximating the first exhaust gas position 112. The diagnostic SCR catalyst element 130 receives a portion of the exhaust gas stream 104 through the exhaust outlet flow path 136. The diagnostic SCR catalyst element 130 is sized to react all or a portion of the $NO_x$ and NH₃ in the exhaust outlet flow path 136. Where the diagnostic SCR catalyst element 130 reacts all of the $NO_x$ and NH₃, until the limiting reagent is consumed, the remaining reagent detected at the composition sensor 132 will be either the remaining $NO_x$ or any remaining NH₃. At many operating conditions, the controller 116 controls reductant injector 114 to provide excess reductant (e.g. from a model of the engine-out $NO_x$, from a detected engine-out $NO_x$ amount, etc.), such that in the exhaust outlet flow path 136 the limiting reagent is $NO_x$ and the composition sensor 132 is determining an excess NH₃ amount.

Where the composition sensor 132 is determining remaining $NO_x$, for example when the NH₃ is the limiting reagent at the diagnostic SCR catalyst 130, an NH₃ deficiency condition 274 may be determined as an expected effect (e.g. when the controller 116 commands the reductant injector 114 to provide less than the reductant required to reduce the engine-out $NO_x$), or the NH₃ deficiency condition 274 may be deduced by a reversal in the expected composition response to a reductant injection increase. In one example, an injection rate increase provides a detected NH₃ decrease, which can then be interpreted as increased $NO_x$ conversion resulting from the reductant injection increase, even where it might have been originally expected that the injection rate increase would result in an increased excess NH₃ amount and thereby a detected NH₃ increase. In certain embodiments, where NH₃ is the limiting reagent and the composition sensor 132 is detecting a $NO_x$ amount, the system 100 includes determining an excess NH₃ amount 248 as a negative value, for example based upon an amount of NH₃ 220 that would need to be provided to reduce the remaining $NO_x$ detected at the sensor 132.

The system includes the compositional sensor 132 disposed in the exhaust outlet flow path 136 at a position downstream of the diagnostic SCR catalyst element 130. The compositional sensor 132 determines NH₃ concentration and/or a $NO_x$ concentration in the exhaust outlet flow path. Certain sensors known in the art have a cross-sensitivity between NH₃ and $NO_x$ determination, and such sensors are usable herein. In certain embodiments, a sensor that determines NH₃ without cross-sensitivity to $NO_x$ may also be utilized as a compositional sensor 132.

In certain embodiments, the system 100 includes the diagnostic SCR catalyst 130 being a micro SCR catalyst and/or a differential SCR catalyst. Where the diagnostic SCR catalyst 130 is a differential catalyst, the diagnostic SCR catalyst 130 reacts only a portion of the incident $NO_x$ and NH₃ during many operating conditions. The concentration of the NH₃ is determinable with a differential catalyst, based partially on an upstream composition value (e.g. from a second composition sensor positioned in the exhaust outlet flow path 136, not shown), a reaction model, or other determination mechanism. The change in concentration of the NH₃, along with the final concentration of NH₃, can be correlated to an excess amount of NH₃, either by reaction rate modeling or by a pre-calibrated model or lookup table. In certain embodiments, the exemplary diagnostic SCR catalyst 130 is sized to react substantially all of the limiting reagent between $NO_x$ and NH₃ present in the exhaust outlet flow path 136.

The controller 116 further includes a response bounding module 210 that computes an actuator response function 250 in response to operating condition(s) 222 of the first SCR catalyst. An exemplary actuator response function 250 includes reductant injector response values 252 as a function of the amount of NH₃ 220, the actuator response function having a response discontinuity. In certain embodiments, the shape and limits of the actuator response function 250 are dynamically calculated in response to the operating condition(s) 222 of the first SCR catalyst.

In certain embodiments, the operating condition(s) 222 of the first SCR catalyst include a current space-velocity of the first SCR catalyst, a flow rate through the first SCR catalyst, a bed temperature of the first SCR catalyst, a $NO_x$ concentration at the first SCR catalyst inlet, an engine torque value, an engine fueling rate, a current NH₃ storage amount, a current NH₃ storage capacity, and/or a current NH₃ storage capacity available. In one embodiment, the bed temperature of the first SCR catalyst 106 is determined without any temperature input from a sensor or estimated temperature value of the exhaust conduit 104 upstream of the first SCR catalyst 106. Another exemplary operating condition includes an inlet temperature of the first SCR catalyst 106, although in certain embodiments, the operating condition(s) 222 exclude any temperature input between the engine 102 and the first SCR catalyst 106.

The controller 116 further includes a dosing amount module 208 that determines a reductant injection amount 260 in response to the amount of NH₃ 220 and the actuator response function 250, and a dosing control module 212 that provides a reductant injector command 232 in response to the reductant injection amount 260.

The exemplary controller 116 further includes an ammonia target module 202 that determines an ammonia reference target 286 that is a target amount of ammonia at the first exhaust gas conduit position. The target amount of ammonia is described in any terms understood in the art, including without limitation a mass of ammonia over a specified time, a concentration of ammonia by mass or volume, or an amount of ammonia relative to an amount of $NO_x$ present in the exhaust conduit (an ammonia to $NO_x$ ratio, ANR). Where the target amount of ammonia is determined in response to a $NO_x$ amount, the $NO_x$ amount may be determined according to NO, $NO_2$, or $NO_x$.

The controller 116 further includes an ammonia error module 206 that determines an ammonia error term 288 in response to the ammonia reference target 286 and the amount of ammonia 220. The ammonia error term 248 may be a difference between the ammonia reference target 286 and the amount of ammonia 220. In certain embodiments, error handling, filtering, and limiting of certain data values, as understood in the art, may cause the ammonia error term 288 to be a value different than the difference between the ammonia reference target 286 and the amount of ammonia 220 during various time periods. In certain embodiments, the ammonia error term 288 is an excess $NH_3$ amount 248 (reference FIG. 2B and the related description) and/or an $NH_3$ deficiency condition 274 (reference again FIG. 2B and the related description).

The dosing amount module 208 further determines the reductant injection amount 260 in response to the ammonia error term 288 and/or the ammonia reference target 286. The ammonia reference target 286 is a value selected from: greater than zero, greater than 5 ppm $NH_3$, less than a stoichiometric ANR, and/or greater than the stoichiometric ANR. In certain embodiments, the ammonia reference target 286 is always a value that is greater than or less than a stoichiometric value, but never equal to a stoichiometric value.

Figure 3A:
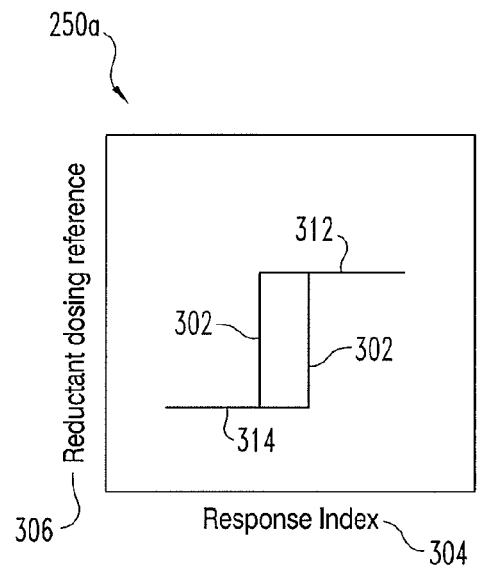
FIGS. 3A-3E are diagrams of various reductant actuator response functions.

Referencing FIG. 3A, a first actuator response function 250a is a binary output of a high response value 312 and a low response value 314 based on a response index 304. The high response value 312 a value greater than a stoichiometric amount of ammonia, such as any value greater than stoichiometric to 2 times stoichiometric. In certain embodiments, the high response value may be three times, four times, five times stoichiometric or even higher. In one example, the high response value is between 1.1 and 1.5 times stoichiometric. The presence of an AMOX catalyst, the operating temperature of the AMOX catalyst, the emissions control scheme and required amount of $NO_x$ reduction for the particular application, as well as other parameters understood in the art will determine appropriate high response values.

In certain embodiments, the high response value 312 is determined as a value greater than a required conversion amount of the SCR catalyst system, in ratios similar to those described. For example, where a modestly capable SCR system is included that requires 30% conversion of the $NO_x$ out of the engine, such as when only 30% is required to meet an emissions standard, the high response value 312 is between 1.1 to 1.5 times the 30%, up to 2 times, 3 times, 4 times, 5 times, or greater than the 30% conversion requirement.

An exemplary high response value 312 is greater than a stoichiometric value 320 (FIG. 3B) plus a confidence interval 254. An exemplary low response value 314 is less than the stoichiometric value 320 minus a confidence interval 254. An exemplary confidence interval 254 is an amount where the measured $NH_3$ is determined to be highly likely to be above (or below) the stoichiometric ANR, after accounting for sensor errors and uncertainty and transient response of sensors and estimators. Exemplary values of the confidence interval 254 include 0.1 ANR, 0.3 ANR, 10 ppm $NH_3$, and 15 ppm $NH_3$. For example, if the exemplary confidence interval 254 is 0.1 ANR on the high side and 0.25 ANR on the low side, the high response value 312 is greater than a 1.1 ANR and the low response value 314 is lower than a 0.75 ANR. The stoichiometric value 320 is an ANR value of 1, or an amount of ammonia that is just sufficient to react all of the $NO_x$ (e.g. NO, $NO_2$, or both) in the exhaust conduit 104. The confidence interval 254 for the high response value 312 may be the same number or a different number than the confidence interval 254 for the low response value 314, and may also change with time or operating conditions 222.

The low response value 314 is a value lower than a stoichiometric amount of ammonia, such as any value lower than stoichiometric to 0.7 times stoichiometric. In certain embodiments, the low response value may be as low as 0.5 or 0.3 times stoichiometric. In one example, the low response value is about 0.9 times stoichiometric. The accuracy of determinations of amounts of ammonia, amounts of $NO_x$, exhaust flow rates, and other estimates and sensed values, as well as the desired rate of consumption of ammonia from the SCR catalyst, will determine appropriate low response values. In certain embodiments, the values of the high response value and the low response value are fixed, and in certain embodiments the values of the high response value and the low response value change as a function of the operating condition(s) 222 of the SCR catalyst.

An exemplary confidence interval 254 for the high response value 312 is a confidence value (e.g. 95% confidence) that, based on estimated errors determining engine $NO_x$ and variability in the reductant injector response relative to the reductant injector command 232, that the actual injected amount will exceed the $NH_3$ reference target 286. An exemplary confidence interval 254 for the low response value 314 is a confidence value (e.g. 95% confidence) that, based on estimated errors determining engine $NO_x$ and variability in the reductant injector response relative to the reductant injector command 232, that the actual injected amount will not exceed the $NH_3$ reference target 286.

An exemplary low response value 314 is less than the stoichiometric value 320 minus a confidence interval 254. The confidence interval 254 includes uncertainties in any measurements or estimates, and is a value that may change over time or operating conditions, for example with degradation of components or during periods where models are uncertain. Exemplary, non-limiting, factors that may affect the confidence interval 254 include the fidelity of engine-out $NO_x$ determinations and $NO/NO_2$ ratio determinations, determinations of conversion of $NO_x$ to $NO_2$ on a catalyst, determinations of the present exhaust flow rate, uncertainty of injected versus commanded reductant amounts, and uncertainties on the hydrolysis rate of urea to $NH_3$.

The response index 304 includes the amount of $NH_3$ 220, but may be a value determined as a function of the amount of $NH_3$, for example and without limitation a concentration, flow rate, normalized value, or an $NH_3$ error term 288 determined by the $NH_3$ error module 206 in response to an $NH_3$ reference target 286 and the amount of $NH_3$ 220.

The first actuator response function 250a includes a response discontinuity 302. The response discontinuity 302 includes at least one range of reductant dosing reference values 306 that are not available as reductant injector responses. The range of not available reductant injector responses at the discontinuity 302 are between a minimum reductant dosing reference (the low response value 314) and a maximum reductant dosing reference (the high response value 312). The minimum reductant dosing reference is the lowest normally occurring dosing reference, the lowest dosing reference the reductant injector is capable of, or a minimal but protective dosing amount of the reductant injector. The maximum reductant dosing reference is the highest normally occurring dosing reference, the highest dosing reference the reductant injector is capable of, the highest reductant injection amount where excessive ammonia does not slip out of the system, or a highest reductant injection amount that still allows reductant injector diagnostics to be performed. Alternatively or additionally, a discontinuity 302 includes a position of the actuator response function that is not continuous (or differentiable)—for example as illustrated with the actuator response function 250d or with the actuator response function 250e in FIGS. 3D and 3E, respectively.

The actuator response function 250a is illustrated with a hysteresis to prevent mode cycling with small fluctuations in the response index 304, but the presence or amount of hysteresis for a given embodiment is a mechanical step for one of skill in the art with the benefit of the disclosures herein. The reductant dosing reference 306 is the target ammonia amount, and the actuator injects reductant to achieve the target ammonia amount. The reductant dosing reference 306 is an amount of $NH_3$ (or precursor such as urea) to inject, a concentration of $NH_3$ for the reductant injector to achieve, and/or an ANR value for the reductant injector to achieve.

Figure 3B:
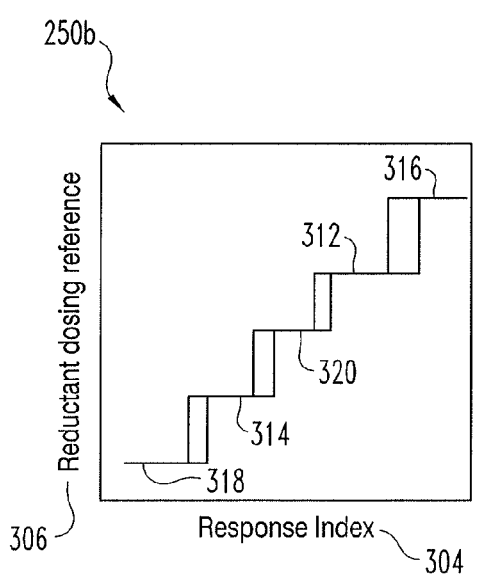
Figure 3C:
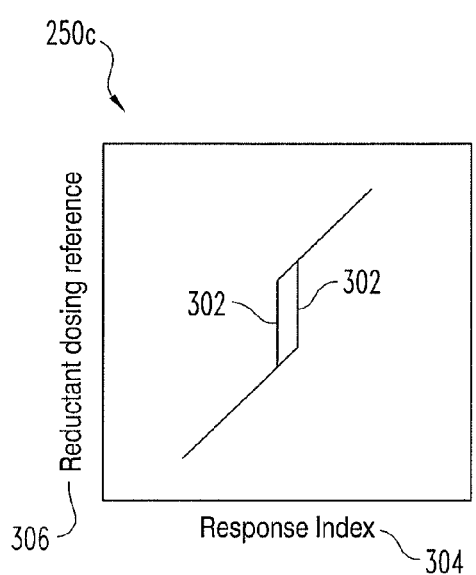
Figures 3D, 3E, 4:
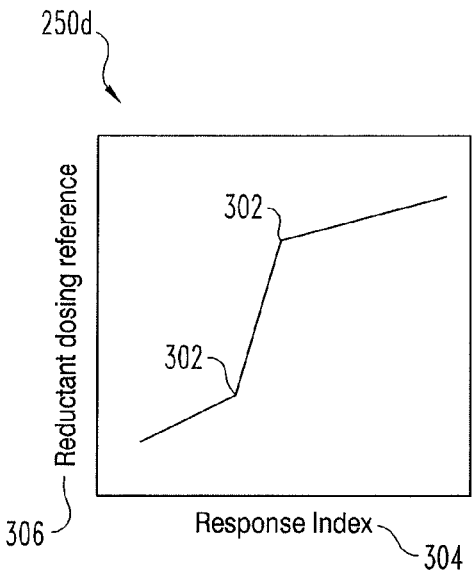
FIG. 4 is a diagram of a response dampening module.

Alternate actuator response functions 250d, 250e are also illustrated in FIGS. 3D and 3E, respectively. The actuator response function 250d exhibits a large center step-change, and the actuator response function 250e exhibits a large center flat response. The implications of each actuator response function 250a, 250b, 250c, 250d, 250e will be understood to those of skill in the art having the benefit of the disclosures herein. While a few exemplary actuator response functions 250 are described, the illustrated actuator response functions 250 are non-limiting, and the illustrated actuator response functions 250 are further not limited to the uses and purposes described herein.

Another actuator response function 250b is illustrated in FIG. 3B. The actuator response function 250b includes a very low response value 318 and a low response value 314, a very high response value 316 and a high response value 312, and a stoichiometric value 320. The stoichiometric value 320 may not be a selectable response value from the actuator response function 250b in certain embodiments, with the actuator response function returning only values of very low, low, high, and very high. The very high response value 316 may be utilized when the response index 304 is very large—for example where the ammonia error term 248 indicates that the desired ammonia reference target 286 is much larger than the amount of $NH_3$ 220. The very low response value 318 may be utilized when the response index 304 is very small—for example where the ammonia error term 288 indicates that the desired ammonia reference target 286 is much smaller than the amount of $NH_3$ 220. In certain embodiments, the very low response value 318 is as low as zero reductant dosing. In certain further embodiments, the very low response value 318 provides for reductant dosing at only a diagnostic amount (i.e. injecting enough to diagnose the reductant injector) or an injector protection amount (e.g. injecting enough to ensure the injector remains clear for injection operations). An exemplary very low response value 318 is a value between zero and 0.3 times a stoichiometric amount of $NH_3$.

In certain embodiments, the discontinuity 302 involves a sharp change of the reductant dosing reference 306 and occurs in the region of a response index value 304 that is consistent with a desired amount of ammonia (e.g. the $NH_3$ reference target 286) at the position 112 between the first SCR catalyst and the second SCR catalyst, which provides for a strong actuator response to offset values from the desired set point. The actuator response 250a is illustrative of the strong actuator response away from the setpoint. By contrast, the actuator response function 250e includes a response having a constant gain with a stoichiometric response value at the discontinuity 302 for a range of response index values 304, which provides for a predictable reductant injection amount. The actuator response 250e may be desirable, for example, where the $NO_x$ amount at the first SCR catalyst inlet and the $NH_3$ injection amounts (the actual reductant injector response to the reductant injector command) are well modeled and feedback control is only desired to correct large offsets from the desired set point.

Referring back to FIG. 3B, the very high response value 316 is a value significantly greater than the high response value 312, and a value of three to five times stoichiometric, or 2.5 to five times stoichiometric, for the very high response value 316 is exemplary and non-limiting. Hysteresis is shown between each reductant dosing reference step (e.g. between very low 318 to low 314), however, some or all of the steps may not have hysteresis, and the amount of hysteresis may differ for each step. The relative sizes of the hysteresis amounts are exemplary. The determination of a very high response value 316 is dependent upon how much $NH_3$ can be injected at the present operating conditions without slipping an unacceptable amount of $NH_3$ out of the system 100. The number of SCR catalysts 106, 108 the presence and size of an AMOX 126, the current operating temperature of the system 100 components, and other determinations known to one of skill in the art contemplating a specific system 100 are factors that determine the very high response value 316.

The reductant dosing reference 306 is utilized to control the reductant doser 114 by any control mechanism understood in the art. The reductant dosing reference 306 may be a feedforward and/or feedback target value, and the control mechanism includes a PID controller, a PI controller, a fuzzy logic controller, or any other type of controller known in the art.

The exemplary controller 116 further includes a response dampening module 216 that dynamically tracks a variability parameter 266, and modifies the actuator response function 250 in response to the variability parameter 266. Exemplary variability parameters and modifications are described. An example includes the variability parameter 266 being a recent error history variability 268 and the response dampening module 216 changes an amplitude of the actuator response function 250 inversely with the recent error history variability 268.

The recent error history variability 268 is any description of error history variability understood in the art. Non-limiting examples include a statistical description of the recent error history such as a standard deviation of a rolling buffer of error terms, a moving average (or a filtered value) of error differences or differentials, a slope of a rolling buffer of error terms, or other description understood in the art. In certain embodiments, for example where the error signal is small or noisy, a target value (e.g. the $NH_3$ reference target 286) or other magnitude reading may be substituted for the error in the recent error history variability 268. For example, the $NO_x$ amount history variability (at any position in the exhaust conduit) or the $NH_3$ reference target 286 variability may be utilized for the variability parameter 266 instead of the error history variability 268.

Exemplary adjustments of an amplitude of actuator response functions 250 are described. An exemplary response dampening module 216 tracks a recent error history variability 268 and changes an amplitude of the response function 250 inversely with the recent error history variability 268. For example, referencing FIGS. 3A to 3E, the amplitude of the actuator response function comprises the relative or absolute (or both) vertical extent of the actuator response function 250A to 250E. In the example of FIG. 3A, where the actuator response function 250a is utilized, the difference between the low response value 314 and the high response value 312 is reduced when the amplitude of the actuator response function 250 is reduced. In the provided example, where the error history variability 268 is decreasing, the amplitude of the actuator response function 250a is increased, and where the error history variability 268 is increasing, the amplitude of the actuator response function 250a is decreased.

Another exemplary response dampening module 216 dynamically tracks a variability parameter 266 as an inlet variability 270 and an outlet variability 272, and the response dampening module 216 decreases an amplitude of the actuator response function 250 when the inlet variability 270 is high and the outlet variability 272 is low. The inlet variability 270 and the outlet variability 272 may be the variability of the flow rate of $NO_x$ or $NH_3$ with respect to time, and/or a variability of a total flow rate in the exhaust conduit at the inlet and/or outlet of any aftertreatment component.

Yet another example includes the variability parameter 266 being an inlet variability 270 and an outlet variability 272, and the response dampening module 216 decreasing the amplitude of the actuator response function 250 when the inlet variability 270 is low and the outlet variability 272 is high. Yet another example includes the variability parameter 266 being an inlet variability 270 and the response dampening module 216 increasing an amplitude of the actuator response function 250 when the inlet variability 270 is high. Still another example includes the variability parameter 266 being an outlet variability 272, and the response dampening module 216 decreases an amplitude of the actuator response function 250 when the outlet variability 272 is high.

The inlet variability 270 and outlet variability 272 may be of an error term 288, an ammonia reference target 286, or other magnitude reading. In certain embodiments, the system includes a second reductant doser positioned between the first and second SCR catalyst (e.g. reference FIG. 6) and the inlet variability 270 and outlet variability 272 is relative to either SCR catalyst 106, 108, and the response dampening module 216 may adjust the amplitude of the response function 250 of reductant injector 114 based on the variability observed for the corresponding SCR catalyst 106, 108.

An exemplary operation for the response dampening module 216 is illustrated in FIG. 4. The inlet variability 270 is a variability parameter 266 of the first SCR catalyst 106 inlet, and the outlet variability 272 is a variability parameter 266 of the first SCR catalyst 106 outlet. The response dampening module 216 provides the actuator modification 256 in response to the values of the inlet variability 270 and the outlet variability 272. In one example, the response dampening module 216 increases an amplitude 258 of the actuator response function 250 when the inlet variability 270 is high and the outlet variability 272 is low. In another example, the response dampening module 216 decreases an amplitude 258 of the actuator response function 250 when the inlet variability 270 is low and the outlet variability 272 is high. In another example, the response dampening module 216 increases an amplitude 258 of the actuator response function 250 when the inlet variability 270 is high. In another example, the response dampening module 216 decreases an amplitude 258 of the actuator response function 250 when the outlet variability 272 is high.

Again referencing FIG. 1A, an apparatus is depicted for controlling dosing of a reductant injector. The apparatus includes diagnostic SCR catalyst element 130 that treats a portion of an exhaust gas stream 104 passing therethrough. The portion of the exhaust gas stream 104 is a portion removed from exhaust outlet flow path 136 at a position downstream of first selective catalytic reduction (SCR) catalyst 106 and upstream of second SCR catalyst 108. The apparatus further includes sensor 132 operationally coupled to the treated portion of the exhaust gas stream and providing a composition signal representative of an $NH_3$ composition of the treated portion. The apparatus includes controller 116 having $NH_3$ determination module 204 (reference FIGS. 2A and 2B) that determines an excess $NH_3$ amount 248 in response to the composition signal 220, and a response bounding module 210 that computes an actuator response function 250 in response to at least one operating condition 222 of the first SCR catalyst 106.

The actuator response function 250 includes a reductant injector response as a function of the excess amount of $NH_3$. Referencing FIG. 3A to 3E, a number of exemplary response functions 250a to 250e are illustrated as a function of excess $NH_3$. In the FIGS. 3A to 3E, the response index 304 is a description of the present value for the excess amount of $NH_3$, which may include an $NH_3$ deficiency condition 274 where the excess amount of $NH_3$ has a negative value. As the excess amount of $NH_3$ rises (or the deficiency present is reducing toward a stoichiometric condition), the response index 304 rises as some function of the excess amount of $NH_3$. The response 250a includes a hysteresis gap on the rising and falling edges of the response index 304. The reductant dosing reference 306 is a value utilized by a dosing controller (e.g. part of injector 116 or another system controller) to determine the target dosing amount of the reductant injector. As the reductant dosing reference 306 rises, the reductant injector command 232 rises as some function of the reductant dosing reference 306.

Figure 2B:
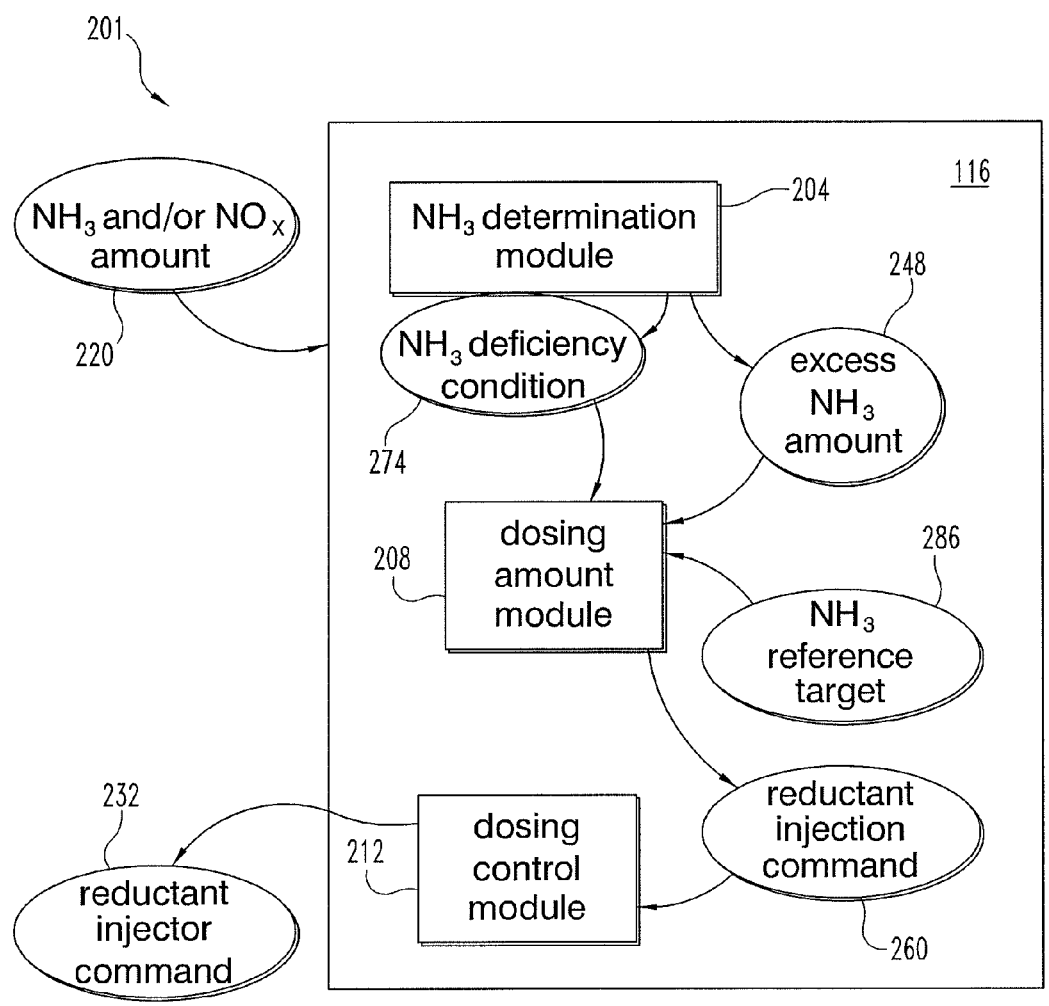
FIG. 2B is a schematic view of a further embodiment of the controller of FIG. 2A.

Referencing FIGS. 2A and 2B, the apparatus further includes a dosing amount module 208 that determines a reductant injection amount 260 in response to the excess amount of $NH_3$ 248 and the actuator response function, and a dosing control module 212 that provides a reductant injector command 232 in response to the reductant injection amount 260.

In certain embodiments, the actuator response function includes a response discontinuity. The apparatus additionally or alternatively includes an ammonia target module 202 that determines an ammonia reference target 286 including a target amount of ammonia at the position downstream of the first selective catalytic reduction (SCR) catalyst and upstream of the second SCR catalyst, an ammonia error module 206 that determines an ammonia error term 288 in response to the ammonia reference target 286 and the excess amount of ammonia 248, and the dosing amount module 208 further determines the reductant injection amount 260 in response to the ammonia error term 288. In certain further embodiments, the ammonia reference target 286 includes an amount greater than zero, greater than 5 ppm $NH_3$, less than a stoichiometric ANR, and greater than the stoichiometric ANR. In certain embodiments, the actuator response function 250 includes a high response value and a low response value, where the high response value includes an ANR ratio greater than a current stoichiometric value, and where the low response value includes an ANR lower than the current stoichiometric value.

In certain embodiments, the dosing amount module 208 further determines the reductant injection amount 260 as only one of the low response value and the high response value, for example such that the reductant injection amount 260 is provided as only a reductant injection amount 260 providing the low response value or a reductant injection amount providing the high response value. In certain embodiments, the actuator response function 250 further includes a very low response value and/or a very high response value, where the very low response value includes a value between 0 and 0.3 times stoichiometric, and where the very high response value includes a value between 2.5 and 5 times stoichiometric. In certain alternative or additional embodiments, each of the low response value and the high response value are dynamically calculated according to the operating condition(s) of the first SCR catalyst.

In certain embodiments, the apparatus further includes a response dampening module 216 that dynamically tracks a variability parameter 266, and modifies the actuator response function 250 in response to the variability parameter 266. An exemplary variability parameter 266, and the modification of the variability parameter 266, includes one or more of the following combinations. A first combination includes the variability parameter 266 as a recent error history variability 268 and the response dampening module 216 changes an amplitude of the actuator response function 250 inversely with the recent error history variability 268. A second combination includes the variability parameter 266 as an inlet variability 270 and an outlet variability 272, and the response dampening module 216 increases an amplitude of the actuator response function 250 when the inlet variability 270 is high and the outlet variability 272 is low. A third combination includes the variability parameter 266 as an inlet variability 270 and an outlet variability 272, and the response dampening module 216 decreases an amplitude of the actuator response function 250 when the inlet variability 270 is low and the outlet variability 272 is high. A fourth combination includes the variability parameter 266 as an inlet variability 270 and the response dampening module 216 increases an amplitude of the actuator response function 250 when the inlet variability 270 is high. A fifth combination includes the variability parameter 266 as an outlet variability 272, and the response dampening module 216 decreases an amplitude of the actuator response function 250 when the outlet variability 272 is high.

The schematic flow descriptions which follow provide illustrative embodiments of performing procedures for controlling $NO_x$ reductant dosing utilizing a micro-SCR catalyst. Operations illustrated are understood to be exemplary only, and operations may be combined or divided, and added or removed, as well as re-ordered in whole or part, unless stated explicitly to the contrary herein. Certain operations illustrated may be implemented by a computer executing a computer program product on a computer readable medium, where the computer program product comprises instructions causing the computer to execute one or more of the operations, or to issue commands to other devices to execute one or more of the operations.

An exemplary procedure includes an operation to receive a portion of an exhaust gas stream into an exhaust outlet flow path, where the portion of the exhaust gas stream is downstream of a first selective catalytic reduction (SCR) catalyst and upstream of a second SCR catalyst. The procedure further includes an operation to treat the removed portion with a diagnostic SCR catalyst element, and an operation to determine a composition of the treated removed portion. The operation to determine the composition includes determining an $NH_3$ concentration. The procedure further includes an operation to determine an actuator response function in response to at least one operating condition of the first SCR catalyst, where the actuator response function includes a reductant injector response as a function of the amount of $NH_3$. The procedure further includes an operation to determine a reductant injection amount in response to the amount of $NH_3$ and the actuator response function, and an operation to inject an amount of reductant upstream of the first SCR catalyst in response to the reductant injection amount.

In certain further embodiments, the actuator response function includes a response discontinuity. In still further embodiments, the actuator response function includes a high response value and a low response value. An exemplary high response value includes an ammonia to $NO_x$ ratio greater than a current stoichiometric value, and an exemplary low response value includes an ammonia to $NO_x$ ratio lower than the current stoichiometric value. Certain further embodiments of the procedure include an operation to determine the reductant injection amount as only one of the high response value and the low response value, and/or an operation to calculate the high response value and the low response value according to the at least one operating condition of the first SCR catalyst.

An exemplary procedure further includes tracking a recent error history variability, the error including a difference between the amount of $NH_3$ and a target amount of $NH_3$, and the procedure further including an operation to change an amplitude of the actuator response function inversely with the recent error history variability.

As is evident from the figures and text presented above, a variety of embodiments according to the present invention are contemplated.

An exemplary set of embodiments is a method including receiving a portion of an exhaust gas stream into an exhaust outlet flow path, where the portion of the exhaust gas stream is downstream of a first selective catalytic reduction (SCR) catalyst and upstream of a second SCR catalyst. The method further includes treating the removed portion with a diagnostic SCR catalyst element, and determining a composition of the treated removed portion, where the determining includes determining an $NH_3$ concentration. The method further includes determining an actuator response function in response to at least one operating condition of the first SCR catalyst, where the actuator response function includes a reductant injector response as a function of the amount of $NH_3$. The method further includes determining a reductant injection amount in response to the amount of $NH_3$ and the actuator response function, and injecting an amount of reductant upstream of the first SCR catalyst in response to the reductant injection amount.

In certain further embodiments, the actuator response function includes a response discontinuity. In still further embodiments, the actuator response function includes a high response value and a low response value. An exemplary high response value includes an ammonia to $NO_x$ ratio greater than a current stoichiometric value, and an exemplary low response value includes an ammonia to $NO_x$ ratio lower than the current stoichiometric value. Certain further embodiments of the method include determining the reductant injection amount as only one of the high response value and the low response value, and/or calculating the high response value and the low response value according to the at least one operating condition of the first SCR catalyst.

An exemplary method further includes tracking a recent error history variability, the error including a difference between the amount of $NH_3$ and a target amount of $NH_3$, and the method further including changing an amplitude of the actuator response function inversely with the recent error history variability.

Another exemplary set of embodiments is an apparatus including a diagnostic SCR catalyst element structured to treat a portion of an exhaust gas stream passing therethrough, where the portion of the exhaust gas stream is a portion removed from an exhaust outlet flow path at a position downstream of a first selective catalytic reduction (SCR) catalyst and upstream of a second SCR catalyst. The apparatus further includes a sensor operationally coupled to the treated portion of the exhaust gas stream and providing a composition signal representative of an $NH_3$ composition of the treated portion. The apparatus further includes an $NH_3$ determination module that determines an excess $NH_3$ amount in response to the composition signal, and a response bounding module that computes an actuator response function in response to at least one operating condition of the first SCR catalyst. The actuator response function includes a reductant injector response as a function of the excess amount of $NH_3$. The apparatus further includes a dosing amount module that determines a reductant injection amount in response to the excess amount of $NH_3$ and the actuator response function, and a dosing control module that provides a reductant injector command in response to the reductant injection amount.

In certain embodiments, the actuator response function includes a response discontinuity. Additionally or alternatively, the apparatus includes an ammonia target module that determines an ammonia reference target including a target amount of ammonia at the position downstream of the first selective catalytic reduction (SCR) catalyst and upstream of the second SCR catalyst, an ammonia error module that determines an ammonia error term in response to the ammonia reference target and the excess amount of ammonia, and the dosing amount module further determines the reductant injection amount in response to the ammonia error term. In certain further embodiments, the ammonia reference target includes an amount greater than zero, greater than 5 ppm $NH_3$, less than a stoichiometric ANR, and greater than the stoichiometric ANR. In certain embodiments, the actuator response function includes a high response value and a low response value, where the high response value includes an ANR ratio greater than a current stoichiometric value, and where the low response value includes an ANR lower than the current stoichiometric value.

Exemplary values for the high and/or low response values are described following. An exemplary low response value is less than the stoichiometric value minus a confidence interval. An exemplary high response value is greater than the stoichiometric value plus a confidence interval. Another exemplary high response value is a value between 1.1 and 2.5 times stoichiometric. Another exemplary low response value includes a value between 0.7 and less than 1 times stoichiometric. Yet another exemplary low response value includes a value between 0.9 and less than 1 times stoichiometric.

In certain embodiments, the dosing amount module further determines the reductant injection amount as only one of the low response value and the high response value, for example such that the reductant injection amount is provided as only a reductant injection amount providing the low response value or a reductant injection amount providing the high response value. In certain embodiments, the actuator response function further includes a very low response value and/or a very high response value, where the very low response value includes a value between 0 and 0.3 times stoichiometric, and where the very high response value includes a value between 2.5 and 5 times stoichiometric. In certain alternative or additional embodiments, each of the low response value and the high response value are dynamically calculated according to the operating condition(s) of the first SCR catalyst.

In certain embodiments, the apparatus further includes a response dampening module that dynamically tracks a variability parameter, and modifies the actuator response function in response to the variability parameter. The variability parameter, and the modification of the variability parameter, includes one or more of the following combinations. A first combination includes the variability parameter as a recent error history variability and the response dampening module changes an amplitude of the actuator response function inversely with the recent error history variability. A second combination includes the variability parameter as an inlet variability and an outlet variability, and the response dampening module increases an amplitude of the actuator response function when the inlet variability is high and the outlet variability is low. A third combination includes the variability parameter as an inlet variability and an outlet variability, and the response dampening module decreases an amplitude of the actuator response function when the inlet variability is low and the outlet variability is high. A fourth combination includes the variability parameter as an inlet variability and the response dampening module increases an amplitude of the actuator response function when the inlet variability is high. A fifth combination includes the variability parameter as an outlet variability, and the response dampening module decreases an amplitude of the actuator response function when the outlet variability is high.

Yet another exemplary set of embodiments is a system including an internal combustion engine, an exhaust conduit fluidly coupled to the internal combustion engine, a first SCR catalyst fluidly coupled to the exhaust conduit, and a second SCR catalyst fluidly coupled to the exhaust conduit at a position downstream of the first SCR catalyst. The system further includes a diagnostic SCR catalyst element structured to treat a portion of an exhaust gas stream passing therethrough, the portion of the exhaust gas stream comprising a portion removed from an exhaust outlet flow path at a position downstream of the first SCR catalyst and upstream of the second SCR catalyst. The system further includes a sensor operationally coupled to the treated portion of the exhaust gas stream and providing a composition signal representative of an $NH_3$ composition of the treated portion, and a reductant doser operationally coupled to the exhaust conduit at a position upstream of the first SCR catalyst, wherein the reductant doser is responsive to a reductant injector command.

The exemplary system further includes a controller having an $NH_3$ determination module that determines an excess $NH_3$ amount in response to the composition signal and a response bounding module that computes an actuator response function in response to an operating condition(s) of the first SCR catalyst, where the actuator response function includes a reductant injector response as a function of the excess amount of $NH_3$. The controller further includes a dosing amount module that determines a reductant injection amount in response to the excess amount of $NH_3$ and the actuator response function, and a dosing control module that provides the reductant injector command in response to the reductant injection amount. In certain embodiments, the operating condition of the first SCR catalyst excludes any temperature input between the engine and the first SCR catalyst.

An exemplary actuator response function includes a high response value and a low response value, where the high response value includes an ANR ratio greater than a current stoichiometric value, and where the low response value includes an ANR lower than the current stoichiometric value. In certain further embodiments, each of the low response value and high response value are dynamically calculated according to the operating condition(s) of the first SCR catalyst. In certain embodiments of the system, there is no $NO_x$ sensor present upstream of the first SCR catalyst and/or there is no $NO_x$ sensor present downstream of the second SCR catalyst. In certain embodiments, there is no ammonia oxidation catalyst present, either downstream of the second SCR catalyst or commingled with the second SCR catalyst. An exemplary system includes the operating condition of the first SCR catalyst being a current space-velocity of the first SCR catalyst, a flow rate through the first SCR catalyst, a bed temperature of the first SCR catalyst, a $NO_x$ concentration at the first SCR catalyst inlet, an engine torque value, an engine fueling rate, a current $NH_3$ storage amount, a current $NH_3$ storage capacity, and/or a current $NH_3$ storage capacity available.

In certain embodiments, the operating condition of the first SCR catalyst includes an inlet temperature of the first SCR catalyst. In certain alternative embodiments, the operating condition(s) of the first SCR catalyst exclude any temperature input between the engine and the first SCR catalyst.

In certain embodiments, the actuator response function includes a response discontinuity. An exemplary system includes the response discontinuity being a range(s) of reductant dosing reference values that are not available reductant injector responses, where the range(s) of reductant dosing reference values are between a minimum reductant dosing reference and a maximum reductant dosing reference. In certain further embodiments, the range of reductant dosing reference values that are not available include a stoichiometric dosing reference.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method, comprising:
    receiving a portion of an exhaust gas stream into an exhaust outlet flow path, wherein the portion of the exhaust gas stream is removed downstream of a first selective catalytic reduction (SCR) catalyst and upstream of a second SCR catalyst that receives a second portion of the exhaust gas stream;
    treating the removed portion with a diagnostic SCR catalyst element;
    determining a composition of the treated removed portion, wherein the determining comprises determining an $NH_3$ concentration;
    determining an actuator response function in response to at least one operating condition of the first SCR catalyst, the actuator response function comprising a reductant injector response as a function of the amount of $NH_3$;
    determining a reductant injection amount in response to the amount of $NH_3$ and the actuator response function; and
    injecting an amount of reductant upstream of the first SCR catalyst in response to the reductant injection amount.

2. The method of claim 1, further comprising tracking a recent error history variability of an error term comprising a difference between the amount of $NH_3$ and a target amount of $NH_3$, the method further comprising changing an amplitude of the actuator response function inversely with the recent error history variability.

3. The method of claim 1, wherein the actuator response function includes a response discontinuity.

4. The method of claim 3, wherein the actuator response function includes a high response value and a low response value, wherein the high response value comprises an ammonia to $NO_x$ ratio greater than a current stoichiometric value, and wherein the low response value comprises an ammonia to $NO_x$ ratio lower than the current stoichiometric value.

5. The method of claim 4, further comprising determining the reductant injection amount as only one of the high response value and the low response value.

6. The method of claim 4, further comprising calculating the high response value and the low response value according to the at least one operating condition of the first SCR catalyst.

7. An apparatus, comprising:
    a diagnostic selective catalytic reduction (SCR) catalyst element structured to treat a portion of an exhaust gas stream passing therethrough, the portion of the exhaust gas stream comprising a portion removed from an exhaust outlet flow path at a position downstream of a first (SCR) catalyst and upstream of a second SCR catalyst;
    a sensor operationally coupled to the treated portion of the exhaust gas stream and providing a composition signal representative of an $NH_3$ composition of the treated portion;
    an $NH_3$ determination module structured to determine an excess $NH_3$ amount in response to the composition signal;
    a response bounding module structured to compute an actuator response function in response to at least one operating condition of the first SCR catalyst, the actuator response function comprising a reductant injector response as a function of the excess amount of $NH_3$;
    a dosing amount module structured to determine a reductant injection amount in response to the excess amount of $NH_3$ and the actuator response function; and
    a dosing control module structured to provide a reductant injector command in response to the reductant injection amount.

8. The apparatus of claim 7, the apparatus further comprising:
    an ammonia target module structured to determine an ammonia reference target comprising a target amount of ammonia at the position downstream of the first selective catalytic reduction (SCR) catalyst and upstream of the second SCR catalyst;
    an ammonia error module structured to determine an ammonia error term in response to the ammonia reference target and the excess amount of ammonia; and
    wherein the dosing amount module is further structured to determine the reductant injection amount in response to the ammonia error term.

9. The apparatus of claim 8, wherein the actuator response function includes a response discontinuity.

10. The apparatus of claim 8, wherein the ammonia reference target is one of: greater than zero, greater than 5 ppm NH$_3$, less than a stoichiometric ANR, and greater than the stoichiometric ANR.

11. The apparatus of claim 8, further comprising a response dampening module structured to dynamically track a variability parameter, and to modify the actuator response function in response to the variability parameter, wherein the variability parameter and modification comprise a combination selected from the combinations consisting of:
  the variability parameter comprises a recent error history variability and the response dampening module is structured to change an amplitude of the actuator response function inversely with the recent error history variability;
  the variability parameter comprises an inlet variability and an outlet variability, and the response dampening module is structured to increase an amplitude of the actuator response function when the inlet variability is high and the outlet variability is low;
  the variability parameter comprises an inlet variability and an outlet variability, and the response dampening module is structured to decrease an amplitude of the actuator response function when the inlet variability is low and the outlet variability is high;
  the variability parameter comprises an inlet variability and the response dampening module is structured to increase an amplitude of the actuator response function when the inlet variability is high; and
  the variability parameter comprises an outlet variability, and the response dampening module is structured to decrease an amplitude of the actuator response function when the outlet variability is high.

12. The apparatus of claim 8, wherein the actuator response function comprises a high response value and a low response value, wherein the high response value comprises an ANR greater than a current stoichiometric value, and wherein the low response value comprises an ANR lower than the current stoichiometric value.

13. The apparatus of claim 12, wherein the low response value is less than the stoichiometric value minus a confidence interval.

14. The apparatus of claim 12, wherein the high response value is greater than the stoichiometric value plus a confidence interval.

15. The apparatus of claim 12, wherein the high response value comprises a value between 1.1 and 2.5 times stoichiometric.

16. The apparatus of claim 12, wherein the low response value comprises a value between 0.7 and 1 times stoichiometric.

17. The apparatus of claim 12, wherein the low response value comprises a value between 0.9 and 1 times stoichiometric.

18. The apparatus of claim 12, wherein the dosing amount module is further structured to determine the reductant injection amount as only one of the low response value and the high response value.

19. The apparatus of claim 12, wherein the actuator response function further comprises at least one of a very low response value and a very high response value, the very low response value comprising a value between 0 and 0.3 times stoichiometric, and the very high response value comprising a value between 2.5 and 5 times stoichiometric.

20. The apparatus of claim 12, wherein each of the low response value and the high response value are dynamically calculated according to the at least one operating condition of the first SCR catalyst.

21. A system comprising:
  an internal combustion engine;
  an exhaust conduit fluidly coupled to the internal combustion engine;
  a first SCR catalyst fluidly coupled to the exhaust conduit;
  a second SCR catalyst fluidly coupled to the exhaust conduit at a position downstream of the first SCR catalyst;
  a diagnostic SCR catalyst element structured to treat a portion of an exhaust gas stream passing therethrough, the portion of the exhaust gas stream comprising a portion removed from an exhaust outlet flow path at a position downstream of the first SCR catalyst and upstream of the second SCR catalyst;
  a sensor operationally coupled to the portion of the exhaust gas stream treated by the diagnostic SCR catalyst element and providing a composition signal representative of an NH$_3$ composition of the treated portion;
  a controller, comprising:
    an NH$_3$ determination module structured to determine an excess NH$_3$ amount in response to the composition signal;
    a response bounding module structured to compute an actuator response function in response to at least one operating condition of the first SCR catalyst, wherein the actuator response function comprises a reductant injector response as a function of the excess amount of NH$_3$;
    a dosing amount module structured to determine a reductant injection amount in response to the excess amount of NH$_3$ and the actuator response function;
    a dosing control module structured to provide a reductant injector command in response to the reductant injection amount; and
  a reductant doser operationally coupled to the exhaust conduit at a position upstream of the first SCR catalyst.

22. The system of claim 21, wherein there is no ammonia oxidation catalyst present downstream of the second SCR catalyst or commingled with the second SCR catalyst.

23. The system of claim 21, wherein the operating condition of the first SCR catalyst comprises at least one condition selected from the conditions consisting of: a current space-velocity of the first SCR catalyst, a flow rate through the first SCR catalyst, a bed temperature of the first SCR catalyst, a NO$_x$ concentration at the first SCR catalyst inlet, an engine torque value, an engine fueling rate, a current NH$_3$ storage amount, a current NH$_3$ storage capacity, and a current NH$_3$ storage capacity available.

24. The system of claim 21, wherein the operating condition of the first SCR catalyst includes an inlet temperature of the first SCR catalyst.

25. The system of claim 21, wherein the at least one operating condition of the first SCR catalyst excludes any temperature input between the engine and the first SCR catalyst.

26. The system of claim 21, wherein there is no NO$_x$ sensor present upstream of the first SCR catalyst.

27. The system claim 26, wherein there is no NO$_x$ sensor present downstream of the second SCR catalyst.

28. The system of claim 21, wherein the at least one operating condition of the first SCR catalyst excludes any temperature input between the engine and the first SCR catalyst.

29. The system of claim 28, wherein the actuator response function comprises a high response value and a low response value, wherein the high response value comprises an ANR greater than a current stoichiometric value, and wherein the low response value comprises an ANR lower than the current stoichiometric value.

30. The system of claim 29, wherein each of the low response value and high response value are dynamically calculated according to the at least one operating condition of the first SCR catalyst.

31. The system of claim 21, wherein the actuator response function includes a response discontinuity.

32. The system of claim 31, wherein the response discontinuity comprises at least one range of reductant dosing reference values that are not available reductant injector responses, wherein the at least one range of reductant dosing reference values are between a minimum reductant dosing reference and a maximum reductant dosing reference.

33. The system of claim 32, wherein the at least one range of reductant dosing reference values includes a stoichiometric dosing reference.

* * * * *